(12) United States Patent
Chilekar et al.

(10) Patent No.: US 8,957,257 B2
(45) Date of Patent: Feb. 17, 2015

(54) PROCESS FOR A CONTINUOUS PRODUCTION OF POLYETHEROLS

(75) Inventors: Vinit Chilekar, Tervuren (BE); Oliver Bey, Niederkirchen (DE); Andreas Brodhagen, Tiefenthal (DE); Achim Loffler, Speyer (DE); Fatemeh Admadnian, Ludwigshafen (DE); Ralf Bohling, Lorsch (DE); Christoph Grossmann, Grunstadt (DE); Ulrich Kammel, Kapellen (BE); Ronald Adelmann, Darmstadt (DE); Thomas Ostrowski, Mannheim (DE); Milind Joshi, Ludwigshafen (DE); Gerrit Waters, Karlsruhe (DE); Dirk Meckelnburg, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 385 days.

(21) Appl. No.: 13/551,936

(22) Filed: Jul. 18, 2012

(65) Prior Publication Data
US 2013/0023700 A1   Jan. 24, 2013

Related U.S. Application Data

(60) Provisional application No. 61/509,121, filed on Jul. 19, 2011.

(51) Int. Cl.
*C07C 41/02* (2006.01)
*C07C 41/03* (2006.01)
(Continued)

(52) U.S. Cl.
CPC ............... *C07C 41/03* (2013.01); *B01J 19/248* (2013.01); *B01J 4/004* (2013.01); *C08G 65/2609* (2013.01); *C08G 65/2696* (2013.01);
(Continued)

(58) Field of Classification Search
USPC .................................. 568/679, 620
See application file for complete search history.

(56) References Cited

U.S. PATENT DOCUMENTS 3,853,986 A * 12/1974 Blass et al. .................... 423/659
5,689,012 A    11/1997 Pazos et al.
(Continued)

FOREIGN PATENT DOCUMENTS

DE    142 809       7/1980
DE    100 54 462 A1    6/2002
(Continued)

OTHER PUBLICATIONS

International Search Report issued Sep. 10, 2012, in PCT/EP2012/063866.
(Continued)

*Primary Examiner* — Rosalynd Keys
(74) *Attorney, Agent, or Firm* — Oblon, Spivak, McClelland, Maier & Neustadt, L.L.P.

(57) ABSTRACT

A process for a continuous production of a polyetherol first involves reacting a catalyst (5) with an alcohol starter (3) or an alkoxylated precursor, to give a mixture comprising an alcoholate and water. Water is then removed from the mixture. The process further involves feeding the alcoholate into a bubble column and feeding an alkylene oxide into the bottom of a compartment of the bubble column, such that the alkylene oxide rises in the alcoholate. The alkylene oxide then reacts with the alcoholate or a secondary product from the reaction between the alcoholate and alkylene oxide, to give the polyetherol.

15 Claims, 2 Drawing Sheets

(51) Int. Cl.
*B01J 19/24* (2006.01)
*B01J 4/00* (2006.01)
*C08G 65/26* (2006.01)

(52) U.S. Cl.
CPC .. *B01J 2219/00768* (2013.01); *B01J 2219/182* (2013.01); *B01J 2219/1943* (2013.01)
USPC .......................................... 568/679; 568/620

(56) References Cited

U.S. PATENT DOCUMENTS

| | | |
|---|---|---|
| 6,410,801 B1 | 6/2002 | Hinz et al. |
| 2002/0147370 A1* | 10/2002 | Hinz et al. .................... 568/620 |
| 2011/0218324 A1 | 9/2011 | Zarbakhsh et al. |
| 2011/0224396 A1 | 9/2011 | Ahmadnian et al. |
| 2011/0224397 A1 | 9/2011 | Ostrowski et al. |
| 2011/0269863 A1 | 11/2011 | Kunst et al. |
| 2011/0282027 A1 | 11/2011 | Deglmann et al. |
| 2012/0116044 A1 | 5/2012 | Kunst et al. |
| 2012/0130134 A1 | 5/2012 | Schopohl et al. |

FOREIGN PATENT DOCUMENTS

| | | |
|---|---|---|
| GB | 736991 | 9/1955 |
| WO | WO 01/36514 A1 | 5/2001 |
| WO | WO 2012/020005 A1 | 2/2012 |
| WO | WO 2012/022048 A1 | 2/2012 |

OTHER PUBLICATIONS

U.S. Appl. No. 13/813,300, filed Jan. 30, 2013, Loeffler, et al.
U.S. Appl. No. 13/817,988, filed Feb. 20, 2013, Kunst, et al.

* cited by examiner

PROCESS FOR A CONTINUOUS PRODUCTION OF POLYETHEROLS

The invention relates to a process for a continuous production of polyetherols in which an alkali metal hydroxide reacts with an alcohol starter or polyalcohol starter or an alkoxylated precursor to give a mixture comprising an alcoholate and water, the water is either partially or completely removed from the mixture or left with the alcoholate for further reaction, and the resulting alcoholate mixture is reacted with alkylene oxides forming the polyetherol.

Polyetherols are an important raw material in the production of polyurethanes. Further, polyetherols are also used as tensides. The production of polyetherols generally is carried out by a catalytic addition of alkaline oxides, particularly propylene oxide and/or ethylene oxide to H-functional starter substances. As a catalyst generally alkali metal hydroxides or salts are used. Of major practical relevance is potassium hydroxide.

In the reaction firstly an alcohol (also called as starter compound) reacts with a base, for example potassium hydroxide, forming the corresponding alcoholate. During this reaction, water is also formed. The water is either partially or completely removed, for example by distillation or stripping or flashing or left within the alcoholate for further reaction, and the alcoholate further reacts with alkylene oxide, for example propylene oxide, ethylene oxide or a mixture of both. The resulting products are mixtures of homologues of different chain lengths.

A continuous process for the production of polyetherols is described for example in DD 142 809. This process is based on potassium hydroxide catalysts and as reactor separate vertically cascaded bubble columns are used. In such a vertically cascaded bubble column reactor, propylene oxide, potassium hydroxide and an alcohol starter are fed to the bottom and the product along with unreacted propylene oxide gas is withdrawn at the top of the column. The cascaded segments in the column lead to a narrow residence time distribution which is required for the narrow molecular weight distribution of the product. To increase the space-time yield of the process it is necessary to run the reaction at higher temperatures and higher pressures. The heat of the reaction of alcoxylation produced in each section due to increased space time yield leads to heat removal limitations due to small specific cooling surface available in the vertical bubble column. The maximum possible internal cooling surface is not sufficient to remove the heat of the reaction completely. There is no possibility of improving the cooling by using other means such as evaporative cooling of propylene oxide. The other problem is that when the entire propylene oxide is added at the bottom of the column, due to high gas loads, there is a non-uniform reaction rate in various sections throughout the height of the column leading to varying cooling duty requirements. This necessitates external heat exchangers in multiple sections in addition to the internal cooling coils making the reactor concept non-economical.

Another reactor concept for the fabrication of polyetherols is disclosed in Mihail Ionescu, *Chemistry and Technology of Polyols for Polyurethanes*, Rapra Technology, pages 120 to 129, 1st Edition, 2005. The reaction is carried out in a batch reactor into which the liquid reaction mass is sprayed in very fine droplets. In the reactor the alkylene oxide, i.e. propylene oxide or ethylene oxide, is contained in gaseous form. Besides reactions in which the liquid is sprayed in very fine droplets also stirred batch reactors are described. After the reaction, the reaction product is purified by removing the catalyst.

A process for forming polyetherols using a spiral reaction tube as a reactor is disclosed in WO-A 01/36514. Another process which uses a tube reactor which is cooled from the outside is disclosed in DE-B 100 54 462.

However it is a disadvantage of all known reactor types being used for the production of polyetherols that increasing the space-time yield of the process is limited by the heat removal capacity of the reactors.

Another problem is to get a narrow residence time distribution along with a uniform reaction throughout the reactor length, needing minimum external heat exchangers.

Therefore, it is an object of the present invention to provide a process for the continuous production of polyetherols which does not exhibit the disadvantages of the known processes.

This object is achieved by a process for continuous production of polyetherols comprising the steps of reacting of an alkali metal hydroxide with an alcohol starter or an alkoxylated precursor to give a mixture comprising an alcoholate and water, removing the water from the mixture, if appropriate, feeding the alcoholate into a bubble column, having an inclination of 0 to 90° to the horizontal, the bubble column being divided into at least two compartments, wherein the compartments are divided from each other by a dividing wall, the dividing wall having a height, that liquid can flow over the dividing wall from one compartment into an adjacent compartment, feeding of alkylene oxide into at least one compartment at the bottom of the compartment such that the alkylene oxide rises in the alcoholate, reacting of the alkylene oxide with the alcoholate or a secondary product being formed by the reaction of the alcoholate with alkylene oxide to give the polyetherol, discharging the reaction product from the horizontal bubble column.

By using a bubble column which has an inclination of from 0 to 90° to the horizontal, it is possible to use the alkylene oxide which is fed into at least one compartment, also for cooling the reaction mixture. The alkylene oxide which does not react collects the heat of the reaction so that the content of the compartment is cooled through evaporative cooling.

Additionally, the bubble column can be cooled by cooling coils or external jacket cooling. The additional cooling coils or external jacket cooling can be limited to individual compartments. Particularly in case sufficient heat can be removed by the alkylene oxide, additional cooling is not needed in this compartment.

If external cooling jackets or cooling coils are used, these also can be used for the initial heating of the reactor during starting-up of the production. For the initial heating, a heating media flows through the external jacket or the internal coil, having a temperature above the temperature which is needed for the start-up of the production. After starting the production and the generation of heat due to the reaction, the heating of the compartments is stopped and if necessary the compartments which comprise external jackets or internal cooling coils are cooled by using a cooling medium which flows through the external jackets or the internal cooling coils.

In a preferred embodiment of the invention, the alkylene oxide is fed into each of the compartments. This has the advantage that additional cooling is not needed in case the flow rate of the alkylene oxide is such that the reaction heat can be removed from the compartments by the alkylene oxide feed. Further, by distributing the alkylene oxide in each of the compartments it is possible to achieve uniform distribution of the alkylene oxide in the compartments. Additionally, it may be possible to adjust the amount of alkylene oxide which is fed into each of the compartments. The amount of alkylene oxide which is fed into each of the compartments may be dependent on the heat which has to be removed from the compartments or the amount of alkylene oxide which is used for the reaction which is carried out in the compartment for forming the polyetherol.

The alkylene oxide can be fed into at least one compartment in gaseous form. However, it is preferred to feed the alkylene oxide into at least one compartment as a liquid. If the alkylene oxide is fed into at least one compartment as a liquid, the alkylene oxide evaporates in the compartment by dissipating the heat of the reaction. Cooling, therefore, can be improved by feeding liquid alkylene oxide into at least one compartment. Particularly, it is preferred to feed alkylene oxide into each of the compartments of the bubble column. The inclination of the bubble column to the horizontal in regard to the present invention is such that each of the compartments of the bubble column can be operated as a separate reactor. Therefore, an inclination in the range of from 0 to 45°, particularly in the range of from 0 to 20° is preferred.

The inclination thereby is such, that in the flow direction of the liquid alcoholate the axis of the bubble column declines. To carry out the reaction, the liquid alcoholate is fed into the bubble column on one side and the reaction mixture which is formed in the bubble column is withdrawn on the other side of the bubble column. Within the bubble column the liquid reaction mixture flows from one compartment to an adjacent compartment over the dividing wall dividing the compartments from each other. In each compartment the reaction mixture further is mixed by feeding the alkylene oxide at the bottom of the compartment by ascension of the alkylene oxide bubbles. Due to the bubbles ascending in each compartment the reaction mixture is fully remixed.

If the bubble column has an inclination of 0° to the horizontal, which means that the orientation of the main axis of the bubble column is in the horizontal, it is preferred that the height of the dividing walls decreases in the flowing direction of the liquid alcoholate. This has the advantage that the liquid alcoholate flows from one compartment to the next compartment and dead zones within the bubble column can be avoided.

Besides feeding the alcohol and the starter or an alkoxylated precursor into the first compartment of the bubble column, it is also possible to feed additionally a starter and/or an alkoxylated precursor into at least one further compartment. This would help in case of products having a mixture of starters with variable alkoxylation degree or it would also be useful for products consisting of a bimodal molecular weight distribution.

The catalyst, which is used for the reaction, preferably is a base. The base is preferably elected from hydroxides of alkali or earth alkali metals, particularly preferable is potassium hydroxide or sodium hydroxide.

The alcohol starter which is used is a monovalent or polyvalent alcohol, particularly a fatty alcohol, oxoalcohol and/or secondary alcohol or a mixture of alcohols. Particularly preferred are low molecular tri-functional alcohols. Particularly preferred as an alcohol are glycerine, propylene glycol, ethylene glycol, trimethylol propane, sorbitol, saccharide. Besides alcohols, further amines like ethylene diamine, triethanol amine or toluene diamine, heptane, alkyl phenol, or natural or synthetic fatty alcohols, fatty amines and hydrogenated amines, fatty amides, fatty acids, sorbitane esters, monoglycerides or monoesterides can be used. Particularly preferred as alcohols are glycerine, propylene glycols and trimethylol propane.

The alkylene oxide which is used for the production of polyetherol is preferably ethylene oxide or propylene oxide. Also mixtures of ethylene oxide and propylene oxide can be used. Further it is possible to use different alkylene oxides simultaneously and/or sequentially wherein in case the alkylene oxides are fed sequentially, different alkylene oxides are fed into different compartments.

Besides ethylene oxide and propylene oxide further butylene oxide can be used. If butylene oxide is used, generally mixtures with ethylene or propylene oxide are used.

In one embodiment of the invention the alkylene oxide is fed into the reactor in form of a mixture comprising the alkylene oxide and nitrogen. Besides nitrogen also other gases that are inert to the reaction can be used. Nitrogen helps in keeping the gas phase concentration of alkylene oxide below the gas phase decomposition limits.

To remove the alkylene oxide which has not reacted with the alcoholate or secondary product it is possible to withdraw the alkylene oxide together with the reaction mixture from the reactor. However, it is preferred to provide a separate outlet for the gaseous components including the alkylene oxide. Particularly, it is preferred to provide the outlet on top of the bubble column so that the gaseous components, comprising the gaseous alkylene oxide, are withdrawn at the top of the reactor. In a preferred embodiment, the gaseous components are cooled to condense the alkylene oxide and recycle the alkylene oxide into the reactor or into a storage tank.

In case a particularly large number of compartments is used for the process, it is preferred to connect at least two bubble columns in series. In this case, the reaction mixture is withdrawn at the end of one bubble column and fed on one side to a next bubble column. Thereby two or more bubble columns can be used.

The invention is described in detail herein below with reference to a drawing.

Figure 1:
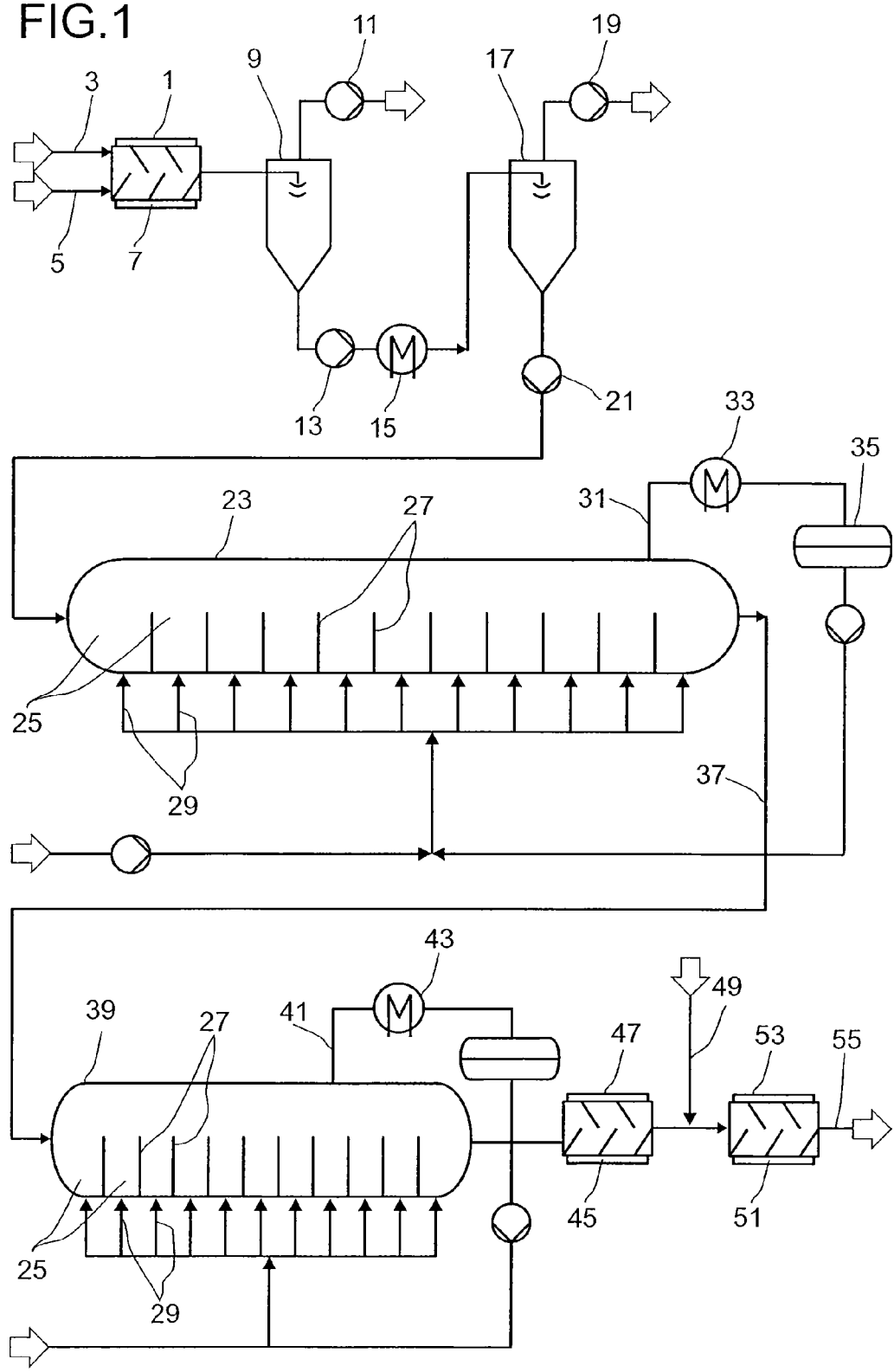
FIG. 1 shows a schematic process flow chart of the inventive process.

A flow chart of the inventive process is shown in FIG. 1.

To a static mixer 1 an alcohol starter 3 and a catalyst 5 are fed. As described above, the alcohol is preferably a low molecular poly-functional alcohol, for example glycerine or trimethylol propane. Further suitable liquid alcohol starters are propylene glycol, ethylene glycol, diethylene glycol, dipropylene glycol, butanediol, or polyetherol, aliphatic amines or aromatic amines such as aniline and amino phenols and their derivatives, ethylenediamine, ethanolamine, diethanolamine, toluene diamine, diphenyl methane diamine, urea, melamine, and its H-functional derivatives and mixtures between aromatic and aliphatic amines, water, alkoxylated alcohols, sorbitol, saccharide, pentaerythritol, cellulose, starch, or sucrose. The catalyst 5 which is fed into the static mixer 1, as a liquid or as an aqueous solution is for example an alkali metal hydroxide or an alkaline earth metal hydroxide, preferably an alkali metal hydroxide, for example sodium hydroxide or potassium hydroxide, particularly potassium hydroxide.

The alcohol starter 3 and the catalyst 5 are mixed in the static mixer 1. In the static mixer 1 the alcohol starter 3 and the catalyst 5 react with each other forming an alcoholate and water. To remove the heat of the reaction, the static mixer 1 can be cooled. For cooling, the static mixer 1 comprises a cooling jacket 7. A heating medium could be fed to the cooling jacket for start-up to achieve the reaction temperature and then the heating medium could be switched to cooling medium in the cooling jacket 7 to provide the required cooling to remove the heat of reaction.

Besides a static mixer 1 any other type of continuous plug flow reactor, for example a tubular reactor or tube bundle reactor, can be used to form the alcoholate from the alcohol and the catalyst.

The reaction mixture which leaves the static mixer 1 is fed into a first flash chamber 9. The reaction mixture being fed into the flash chamber 9 has a temperature preferably between 100 and 150° C., particularly a temperature in the range of from 120 to 140° C. The pressure in the first flash chamber 9 is in the range from 100 to 1000 mbar, preferably in the range of 150 to 500 mbar, particularly preferred in the range of from 150 to 250 mbar.

To set the vacuum in the flash chamber 9, a vacuum pump 11 is provided. In the flash chamber 9 the water from the catalyst and the reaction water contained in the reaction mixture evaporates and is removed from the flash chamber 9 via the vacuum pump 11.

The remaining alcoholate comprising mixture is withdrawn at the bottom of the first flash chamber 9, pumped by a pump 13 and heated in a heat exchanger 15. With the pump 13 the alcoholate comprising mixture is compressed to a pressure in the range from 3 to 10 bar, preferably in the range of from 4 to 8 bar and particularly in the range from 5 to 7 bar. The mixture is heated in the heat exchanger 15 to a temperature in the range from 100 to 180° C., preferably in the range of from 120 to 160° C. and particularly in the range of from 125 to 150° C.

In the embodiment as shown in FIG. 1, the alcoholate comprising mixture is fed into a second flash chamber 17. The second flash chamber 17 also comprises a vacuum pump 19 with which the pressure in the flash chamber 17 is reduced to 10 to 200 mbar, preferably to the range from 20 to 100 mbar, particularly in the range of 30 to 80 mbar. In the second flash chamber 17 remaining water from the alcoholate comprising reaction stream is removed and withdrawn via the second vacuum pump 19. In a pump 21 the alcoholate being essentially free from water is compressed to pressure in the range of from 3 to 10 bar, preferably in the range of from 4 to 8 bar, particularly in the range of from 5 to 7 bar.

In regard to the present invention essentially free from water means that the amount of water in the alcoholate comprising stream is at most 1 wt-%, preferably at most 0.1 wt-% and particularly 0.05 wt-%.

The alcoholate stream being essentially free from water is fed into a first bubble column 23. According to the invention, the first bubble column 23 is inclined to the horizontal at an angle of 0° to 90°, preferably at an angle of 0° to 45° and particularly at an angle of 0° to 20°. In the embodiment as shown in FIG. 1, the inclination to the horizontal is 0°.

Optionally, the alcoholate stream could also be fed to a continuous stirred tank reactor (CSTR) where it is reacted with at least 1 to 30 moles of alkylene oxide per mole of alcoholate before feeding it to the first bubble column.

The first bubble column is divided into several compartments 25 by dividing walls 27. The height of the dividing walls 27 is such that liquid from one compartment 25 can flow into an adjacent compartment over the dividing wall.

In the embodiment as shown in FIG. 1 each compartment 25 is furnished with a gas distributor 29, which is shown schematically by an arrow. Via the gas distributors 29 alkylene oxide, preferably propylene oxide or ethylene oxide is fed into the compartments 25. The alkylene oxides can be fed as a liquid or as a gas. In one embodiment of the invention it is preferred to feed liquid alkylene oxide into the compartments 25. The liquid alkylene oxide provides evaporative cooling in the compartments 25 by taking out the reaction heat by evaporation of the alkylene oxide. After being fully evaporated, the gaseous alkylene oxide will be further heated by taking up heat from the reaction. If the alkylene oxide is fed in gaseous state the amount of heat which can be absorbed by the alkylene oxide is much less than when feeding liquid alkylene oxide. In one embodiment of the invention the alkylene oxide is fed in a mixture with an inert gas into the compartments 25. By feeding an additional inert gas it is possible to feed a larger amount of gas and therefore achieve a better mixing effect within the compartments.

The gas, i.e. alkylene oxide and optionally inert gas, which has not reacted with the alkoxylate forming polyetherol, is collected on top of the bubble column 23. On the top of the bubble column 23 an outlet line 31 is provided through which the gaseous alkylene oxide and optionally inert gases are removed from the first bubble column 23. The gaseous components are cooled and if appropriate partially condensed in a heat exchanger 33.

The heat exchanger 33 is followed by a gas-liquid separator 35. In the gas-liquid separator 35 components which have been condensed in the heat exchanger 33 are separated from the components remaining in gaseous form. The condensed parts essentially comprise alkylene oxides.

In the embodiment as shown in FIG. 1, the alkylene oxide is recycled into the first bubble column 23 or back to the alkylene oxide supply tank. Further it is also possible to recycle a fraction of the stream to the first bubble column 23 and to send the rest to the alkylene oxide storage tank.

The resulting reaction mixture comprising polyetherol is withdrawn from the first bubble column 23 via an outlet line 37. The outlet line 37 and the feed line through which the alcoholate is fed into the bubble column 23 are arranged on opposite sides of the first bubble column 23 such that the liquid flows from the feeding point to the outlet line 37.

In the embodiment as shown in FIG. 1, the first bubble column 23 is followed by a second bubble column 39. The second bubble column essentially is designed in a similar way as the first bubble column 23. The second bubble column 39 is also inclined with an angle of 0 to 90° to the horizontal, preferably with an angle of 0 to 45° and particularly with an angle of 0 to 20° to the horizontal. The second bubble column 39 also is divided into compartments 25 by dividing walls 27. Into the compartments 25 of the second bubble column 39 gaseous alkylene oxide is fed via gas distributors 29. Further, not reacted alkylene oxide is withdrawn from the second bubble column 39 via an outlet line 41, cooled in a heat exchanger 43 and recycled into the second bubble column 39.

Depending on the polyetherol, which is produced, it is possible to feed different alkylene oxides into the first bubble column and the second bubble column 39. For example it is possible to feed ethylene oxide into the first bubble column 23 and propylene oxide into the second bubble column 39. Also propylene oxide can be fed into the first bubble column 23 and ethylene oxide into the second bubble column 39. However, it is also possible to feed the same alkylene oxide, for example ethylene oxide or propylene oxide, or a mixture of both, into each of the bubble columns 23, 39.

The bubble columns and the compartments in the bubble columns can all have the same size or can be of different sizes. Generally, the compartments in one bubble column will have the same size. However, it is also possible that the size of the compartments decreases in flow direction of the liquid components or that the size of the compartments increases in the flow direction of the liquid components. In a preferred embodiment the size of the compartments 25 increases in flow direction of the liquid components.

Besides the embodiment as shown in FIG. 1, in which into each compartment of the bubble columns 23, 39, alkylene oxide is fed, it is possible that the alkylene oxide only is fed into several compartments, for example in every second compartment. Further, it is also possible to feed the alkylene oxide only into the first compartment of the horizontal bubble column and for example inert gases into the additional compartments. However, it is preferred to feed alkylene oxide into each of the compartments of the bubble columns 23, 39.

After leaving the second bubble column 39, the polyetherol comprising reaction mixture can be fed into a post reactor 45.

The post reactor 45 can be for example a tubular reactor, which may have static mixer elements. In the post reactor 45 the reaction forming the polyetherol is completed by reacting away at least 90% of the free alkylene oxide entering the post reactor 45. To remove reaction heat from the reactor, the reactor can be furnished with a cooling jacket 47.

In the embodiment as shown in FIG. 1 additional alkylene oxide is fed via a feeding line 49 into the reaction mixture leaving the post reactor 45. After adding the alkylene oxide via the feeding line 49, the mixture is fed into a further tubular reactor 51 which is also furnished with static mixer elements and a cooling jacket 53 for removing heat of the reaction. The polyetherol comprising product stream is withdrawn from the tube reactor 51 via a product outlet line 55. If an additional feeding line 49 is used as shown in FIG. 1, the alkylene oxide which is fed via the feeding line 49 preferably is different from the alkylene oxide being fed into the first and second bubble columns 23, 39. Besides the embodiment as shown in FIG. 1, comprising two flash chambers 9, 17 it is also possible only to use one flash chamber for removing the water. However, using two flash chambers, as shown in FIG. 1, leads to an alcoholate feeding stream, which comprises less water. Besides a flash chamber, also every other standard distillation or stripping unit generally used can be employed.

Further, if the polyetherol which is withdrawn from the bubble column 23 or 39 corresponds to the desired specification, it is not necessary to use the second bubble column 39 or the post reactor 45 or the tube reactor 51. The product stream could by-pass the reactors and directly be stripped free of alkylene oxide in the stripping columns. It would also be possible to use parallel post reactors with addition of more alkylene oxide streams.

If a post reactor 45 is used, this reactor can be a tubular reactor with static mixers as shown in FIG. 1 or any suitable reactor which can be used for completing the reaction. Beside the tube reactor 51, also each continuous reactor, which is suitable to perform the reaction, can be used. Reactor types which can be used as post reactor 45 or reactor 51 are for example tube bundle reactor, compartment reactor, cascade of stirrer tanks, coil reactors, spiral tubes, jet loop reactor, micro reactors, or partitioned continuous stirred tank reactors and plug flow reactors.

Figure 2:
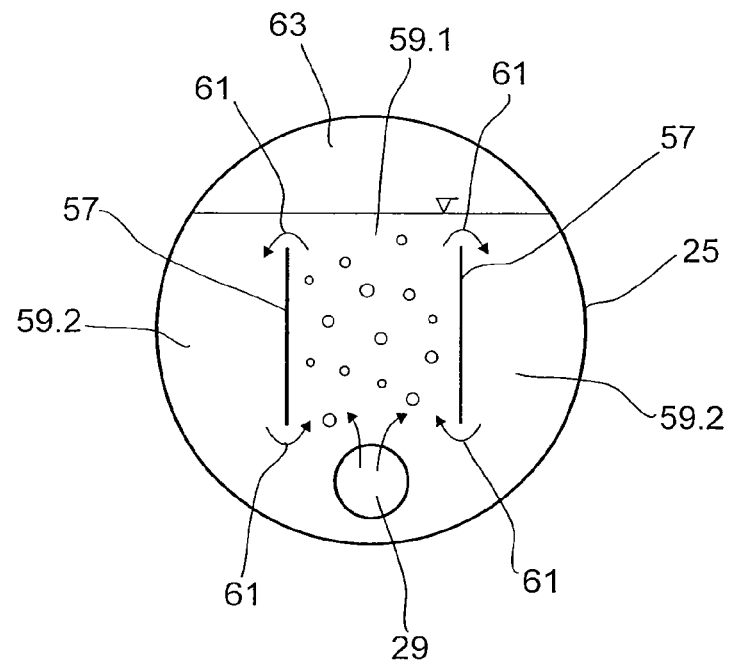
FIG. 2 shows a cross-section of the bubble column in a first embodiment.

FIG. 2 shows a cross section of one compartment of the bubble column in a first embodiment. At the bottom of the compartment 25 the gas distributor 29 is arranged. In the compartment 25 two vertical baffles 57 are arranged, which divide the compartment 25 into three sections 59. The alkylene oxide distributor 29 is positioned in the middle of the compartment and therefore in the middle section 59.1. By feeding alkylene oxide via the distributor into the middle section 59.1 a fluid flow is generated. The liquid flows from the middle section 59.1 over the upper edge of the vertical baffles 57 into the outer sections 59.2. Further, the liquid flows around the lower edges of the vertical baffles 57 back into the middle section 59.1. The flow of the liquid is shown with arrows 61. The position of the distributor and the vertical baffles 57 inside the compartment 25 results in a jet loop reactor.

Figure 3:
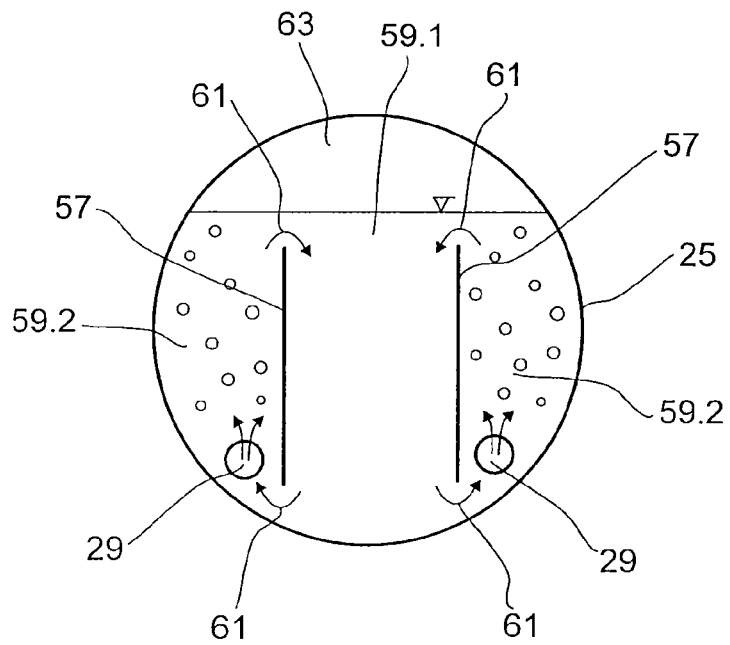
FIG. 3 shows a cross-section of the bubble column in a second embodiment.

In FIG. 3 a second embodiment of a compartment of the bubble column is shown. The embodiment as shown in FIG. 3 differs from FIG. 2 in the position of the gas distributor 29. Instead of one gas distributor 29 arranged in the middle section 59.1, according to FIG. 3, two gas distributors 29 are provided which are arranged in the outer sections 59.2. Feeding gas into the outer sections 59.2 also leads to a fluid flow, however, the liquid flows in the outer sections 59.2 upwards and around the upper edge of the vertical baffles 27 into the middle section 59.1. The liquid flows in the middle section 59.1 downwards and around the lower edges of the vertical baffles 57 again into the outer sections 59.2.

In the embodiments in FIG. 2 and FIG. 3 the alkylene oxide is fed as liquid or as a gas. The liquid evaporates taking away the heat of reaction, generating gas that rises through the liquid generating the convection flow required for the necessary mixing in the reaction chamber. The gas partially gets dissolved in the reaction mixture as it rises and reacts with the alkoxylated product and the gas which has not reacted with the liquid in the compartment 25 is collected at the top of the compartment 25 forming a gas space 63. From the gas space 63 the gas is removed via the outlet line 31 or 41.

Besides the embodiments as shown in FIGS. 2 and 3 comprising two vertical baffles 57 in each compartment, it is also possible to arrange more than two baffles 57 or just one baffle 57 in the compartment 25. The number of vertical baffles 57 mainly depends on the diameter of the bubble column 23, 39. Further, the bubble column 23, 39 does not necessarily need a circular cross section as shown in FIG. 2 and FIG. 3. Beside a circular cross section also any other form is possible. However, it is preferred to have a cross section having a shape without any edges. Therefore, besides a circular cross section also oval cross sections are preferred.

In an alternative embodiment, bubble column (23, 39) is provided with internal coils in each section to provide additional cooling required in case the evaporative cooling is not sufficient to remove the heat of reaction. The internal coils can be placed in the sections 59.1 or 59.2 or in both sections 59.1 and 59.2 to provide a larger cooling surface for removal of heat.

Further it is possible to provide at least one tubular reactor following the first bubble column 23. This at least one tubular reactor is followed by the second bubble column (39), the post reactor and the second reactor.

LIST OF REFERENCE NUMERALS

1 static mixer
3 alcohol
5 catalyst
7 cooling jacket
9 flash chamber
11 vacuum pump
13 pump
15 heat exchanger
17 second flash chamber
19 second vacuum pump
21 pump
23 first bubble column
25 compartment
27 dividing wall
29 gas distributor
31 outlet line 33 heat exchanger
35 liquid precipitator
37 outlet line
39 second bubble column
41 outlet line
43 heat exchanger
45 secondary reactor
47 cooling jacket
49 feeding line
51 tube reactor
53 cooling jacket
55 product outlet line
57 vertical baffle
59 section
59.1 middle section
59.2 outer section
61 liquid flow
63 gas space

The invention claimed is:

1. A process for a continuous production of polyetherols comprising the steps of
   reacting a catalyst (5) with an alcohol starter (3) or an alkoxylated precursor to give a mixture comprising an alcoholate and water,
   removing the water from the mixture by distillation, if appropriate,
   feeding the alcoholate into a bubble column (23), having an inclination of from 0 to 90° to the horizontal, the bubble column (23) being divided into at least two compartments (25), wherein the compartments (25) are divided from each other by a dividing wall (27), the dividing wall (27) having a height, that liquid can flow over the dividing wall (27) from one compartment (25) into an adjacent compartment,
   feeding of alkylene oxide into at least one compartment (25) at the bottom of the compartment such that the alkylene oxide rises in the alcoholate,
   reacting of the alkylene oxide with the alcoholate or a secondary product being formed by the reaction of the alcoholate with alkylene oxide to give the polyetherol,
   discharging the reaction product from the bubble column (23).

2. The process as claimed in claim 1, wherein the alkylene oxide is fed into each of the compartments (25).

3. The process as claimed in claim 1, wherein the alkylene oxide is fed into at least one compartment (25) in gaseous form.

4. The process as claimed in claim 1, wherein the alkylene oxide is fed into at least one compartment (25) as a liquid and evaporates in the compartment (25).

5. The process as claimed in claim 1, wherein the bubble column (23) has an inclination such that in flowing direction of the liquid alcoholate the axis of the bubble column declines.

6. The process as claimed in claim 1, wherein the height of the dividing walls (27) decreases in the flowing direction of the liquid alcoholate.

7. The process as claimed in claim 1, wherein starter and/or alkoxylated precursor is additionally fed into at least one further compartment.

8. The process as claimed in claim 1, wherein the catalyst is a base.

9. The process as claimed in claim 8, wherein the base is elected from hydroxides of alkali or earth alkali metals.

10. The process as claimed in claim 1, wherein the alcohol is low-molecular trifunctional alcohol.

11. The process as claimed in claim 1, wherein the alkylene oxide is ethylene oxide or propylene oxide.

12. The process as claimed in claim 1, wherein a mixture comprising the alkylene oxide and nitrogen is fed into the bubble column.

13. The process as claimed in claim 1, further comprising the step of withdrawing gaseous components, comprising gaseous alkylene oxide, at the top of the bubble column (23), cooling the gaseous components to condense the alkylene oxide and recycle the alkylene oxide into the bubble column (23) or a storage tank.

14. The process as claimed in claim 1, wherein in at least one compartment (25) at least one vertical baffle (57) is arranged, the vertical baffle (57) dividing the compartment into sections wherein the vertical baffles (57) are designed such that there is a space between an upper edge of the vertical baffle (57) and the jacket of the bubble column (23) and a space between a lower edge of the vertical baffle (57) and the jacket of the bubble column (23) such that liquid can flow around the baffle (57), and wherein gas distributors (29) by which the alkylene oxide is fed into the compartment (25) are arranged such that every second section is furnished with a gas distributor (29).

15. The process as claimed in claim 1, wherein at least two bubble columns (23, 39) are connected in series.

* * * * *

UNITED STATES PATENT AND TRADEMARK OFFICE
CERTIFICATE OF CORRECTION

PATENT NO. : 8,957,257 B2
APPLICATION NO. : 13/551936
DATED : February 17, 2015
INVENTOR(S) : Vinit Chilekar et al.

It is certified that error appears in the above-identified patent and that said Letters Patent is hereby corrected as shown below:

On the title page, Item (75), the Inventors' Information should read:

--(75) Inventors: Vinit Chilekar, Tervuren (BE);
Oliver Bey, Niederkirchen (DE);
Andreas Brodhagen, Tiefenthal (DE);
Achim Loeffler, Speyer (DE);
Fatemeh Ahmadnian, Ludwigshafen (DE);
Ralf Boehling, Lorsch (DE);
Christoph Grossmann, Gruenstadt (DE);
Ulrich Kammel, Kapellen (BE);
Ronald Adelmann, Darmstadt (DE);
Thomas Ostrowski, Mannheim (DE);
Milind Joshi, Ludwigshafen (DE);
Gerrit Waters, Karlsruhe (DE);
Dirk Meckelnburg, Limburgerhof (DE)--

Signed and Sealed this
Ninth Day of June, 2015

Michelle K. Lee
*Director of the United States Patent and Trademark Office*